United States Patent [19]
Watson

[11] 3,978,286
[45] Aug. 31, 1976

[54] ARTIFICIAL LARYNX

[76] Inventor: Bernard William Watson, 60A Meadway, Harpendon, Hertfordshire, England

[22] Filed: Oct. 18, 1974

[21] Appl. No.: 515,899

[30] Foreign Application Priority Data

Oct. 31, 1973 United Kingdom .............. 50587/73

[52] U.S. Cl. .............................................. 179/1 AL
[51] Int. Cl.[2] ........................ A61F 1/20; Q10L 1/10
[58] Field of Search ............ 179/1 Al; 3/1.3; 74/25; 340/390

[56] References Cited

UNITED STATES PATENTS

| | | | |
|---|---|---|---|
| 1,172,712 | 2/1916 | Hutchinson | 340/390 |
| 2,056,295 | 10/1936 | Riesz | 3/1.3 |
| 2,058,212 | 10/1936 | Burchett | 3/1.3 |
| 2,916,920 | 12/1959 | Planer et al. | 74/25 |
| 3,072,745 | 1/1963 | Barney | 179/1 AL |
| D190,812 | 5/1877 | Boren | D26/14 |

*Primary Examiner*—Kathleen H. Claffy
*Assistant Examiner*—E. Matt Kemeny
*Attorney, Agent, or Firm*—Hill, Gross, Simpson, Van Santen, Steadman, Chiara & Simpson

[57] ABSTRACT

A speech aid device has a housing with a tubular main body enclosing a battery and an electric motor. An obliquely directed side arm of the housing has a diaphragm resiliently mounted at the free end. A striker is guided for reciprocable movement along the side arm axis to beat against the other face of the diaphragm and is driven by the motor through a gear box and an eccentric drive. A tension spring is included in the drive and a compression spring opposes the striker return movement, so that the striker is floatingly mounted by the springs. A feature of the drive is a resilient link between the motor and hammer.

11 Claims, 2 Drawing Figures

ARTIFICIAL LARYNX

Figures 1, 2:
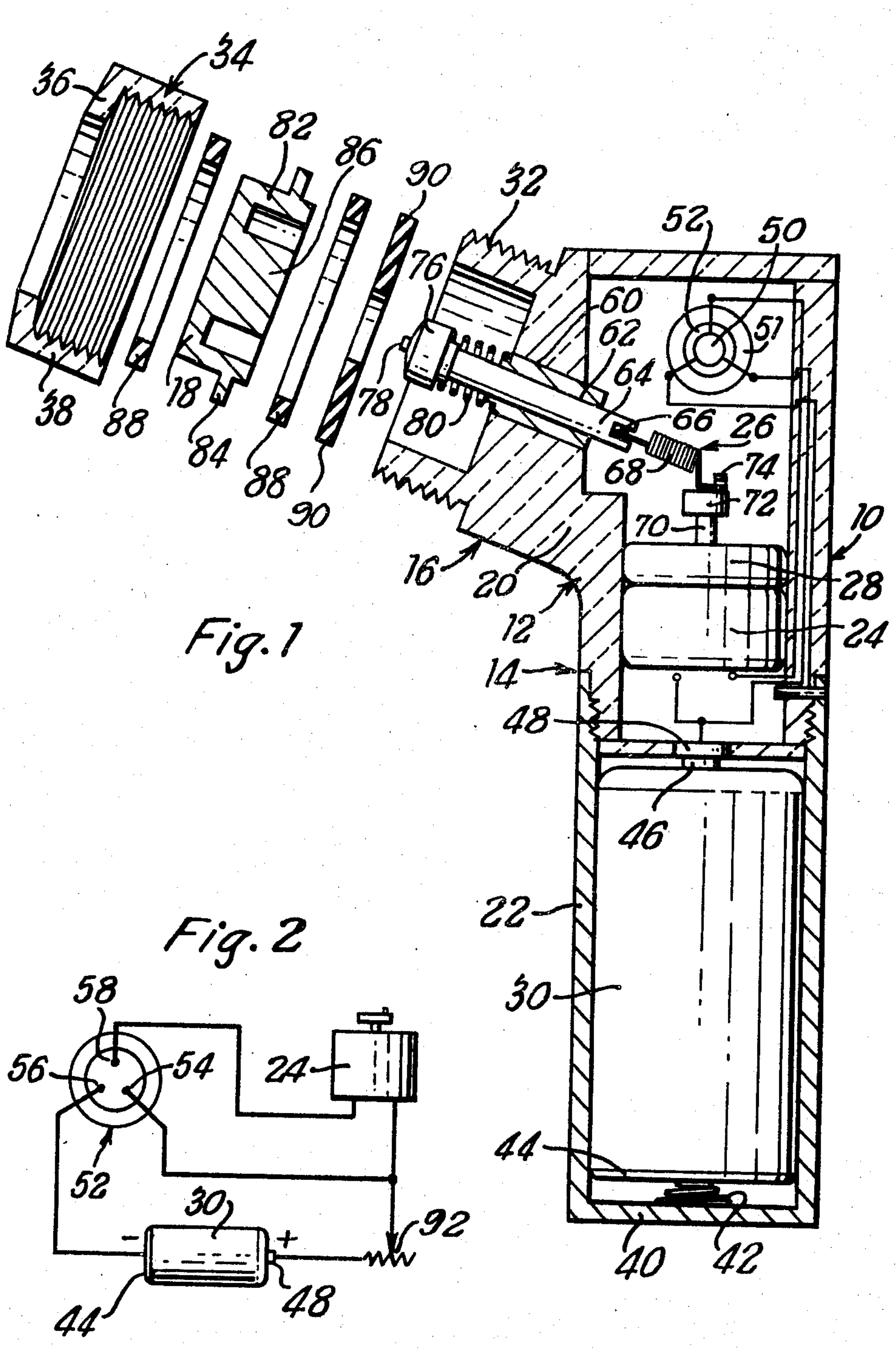

The invention relates to speech aid devices.

Normal speech requires selective adjustment of the shape of the mouth in order to modify sound produced by the vocal chords. Where, by disease or removal of the larynx a patient has been reduced to aphonia, speech may be simulated provided vibrations of a suitable frequency are applied to the throat from an external source.

An object of the invention is to provide a speech aid or vibrator device which can function as a convenient external source of such vibrations.

It is a further object of the invention to provide an electro-mechanical speech aid device which is simple in construction and reliable in operation.

It is another object of the invention to provide a speech aid vibrator device having diaphragm means actuated mechanically by a striker mechanism including a striker floatingly mounted by spring means.

A feature of the invention is the provision of a speech aid device comprising a diaphragm for location adjacent to a users throat, and means for mechanically vibrating the diaphragm at an appropriate frequency. Another feature of the invention is that the striker or vibrating means comprises a hammer arranged to strike the diaphragm, and in an advantageous arrangement, the hammer is reciprocated at right angles to the plane of the diaphragm. Both the hammer and the diaphragm are preferably resiliently mounted, the former for example being mounted by means of one or more springs and the latter by being held in resilient material. The drive to the hammer can be obtained from a battery-powered electric motor, a spring being connected between one end of the reciprocable hammer and an eccentric connection on the motor drive shaft.

By way of illustration, a speech aid device embodying the invention is described below with reference to the accompanying drawing, in which:

FIG. 1 is a sectional side view of the speech aid device embodying the invention; and, FIG. 2 is a circuit drawing illustrating the electrical arrangements of the speech aid device of FIG. 1.

The illustrated device 10 has a housing 12 consisting of a main tubular portion 14 and a side arm portion 16 at or near one end thereof, the axis of the side arm portion making an obtuse angle preferably of 110° with that of the main tubular portion. As will be further described below, a mechanically actuated diaphragm 18 is mounted at the free end of the side arm portion 16 and this arrangement of the housing readily allows the diaphragm to be placed against a users throat, the main tubular portion 14 being used as handle.

The main tubular portion 14 comprises a body 20, suitably moulded from a relatively rigid plastics material, for example that known by the trade mark Perspex, having the side arm portion at one end, and a hollow casing 22 of the same cross-section extending from the other end. The body 20 contains an electric motor 24 and a hammer drive arrangement 26 which the motor is arranged to drive through a gear box 28. The casing 22 contains a battery 30 providing power for the motor. The side arm 16 is formed integrally with the body 20 and has an externally threaded free end 32. A cap 34, which may be of the same material as the body, has an annular portion 36 and an internally threaded skirt portion 38 received on the threaded free end of the side arm portion 16. The end of the body 20 remote from the side arm portion is also externally threaded for connection to the casing 22, so that this can be readily removed and replaced when a new battery is required. The battery casing 22 which may conveniently be of aluminium has a closed end 40 forming the end of the main tubular portion, and a spring 42 is received between the closed and and the battery 30, to ensure good electrical contact between the casing and the terminal 44 at the lower end of the battery, and also between a terminal 46 at the other end of the battery and a fixed terminal 48 mounted at the adjacent end of the body.

The wall of the body is apertured at a position adjacent the side arm portion to receive a button 50 for operation of a microswitch 52 mounted internally of the body on the wall and connected to control energisation of the motor 24. To reduce the possibility of unintentional operation, the wall is preferably dished at 51 or otherwise shaped around the aperture so that the button does not project outwardly beyond the general shape of the wall. It will be seen from FIG. 2 that the battery positive terminal 48 is connected both to the motor and to a switch terminal 54. The negative terminal 44 is connected to a second switch terminal 56 and a third switch terminal 58 is connected to the other terminal of the motor. In the normal position of the switch, terminals 54 and 58 are connected together but isolated from the terminal 56, so the motor does not operate.

Depression of the button 50 actuates the switch to break the connection between the terminals 54 and 56 and to complete the return path from the motor to the negative terminal of the battery through the switch terminals 58 and 56, so that the motor turns. Release of the button breaks the connection between the terminals 58 and 56 and restores the connection between the terminals 54 and 58. The motor coil is thus shorted through the switch so that the motor is brought quickly to a stop. A user of the device can thus cut off the sound source very sharply, which greatly facilitates speech simulation.

The side arm portion 16 at its junction with the main tubular portion 14 will be seen to have a wall portion with an aperture 60 along the side arm axis which aperture opens outwardly at the side arm portion free end and into the interior of the body. In the aperture is secured a tubular bearing 62 for example of PTFE (polytetrafluoroethylene) in which a striker or hammer shaft 64, suitably of steel, is slidably received. An end of the shaft extends within the body 20 and is formed with a slot across which a pin 66 extends for connecting the shaft to one end of a tension spring 68 forming part of the hammer drive arrangement 26. An output drive spindle 70 of the gear box 28 extends axially of the main tubular portion 14 away from the motor 24 and a bushing 72 mounted on this drive spindle has an eccentric stud 74 extending parallel to the spindle. The other end of the tension spring 68 is connected to this stud 74. At the outer end, the hammer shaft 64 carries a hammer head 76 suitably of tufnol, having a free end tapering to a short central protrusion 78 for engaging the diaphragm 18. The head 76 is of greater diameter than the shaft and a compression spring 80 is trapped between the head and the bearing 62, so that the hammer, comprising the shaft 64 and the hammer head 76, is floatingly mounted for axial reciprocation as the electric motor rotates the bushing 72.

Between the outer end of the side arm and the cap 34, the diaphragm 18 is held in resilient mounting means in a position to be repeatedly struck by the hammer head protrusion 78 as the device 10 is operated. The diaphragm 18 which may for example be moulded in Bakelite has a short integral skirt portion 82 with an external flange 84. A central boss 86 extends from the diaphragm within the skirt to function as an anvil to be struck by the hammer protrusion 78. The external flange 84 is received between a pair of washers 88 of foam rubber or other resilient material of suitable compressibility, the washers being themselves clamped between the outer end of the side arm and the annular portion 36 of the cap 34, the outer surface of the diaphragm 18 being then slightly outward of the cap. A third resilient washer 90 can be provided adjacent the outer end of the side arm portion 16.

In use, the device is held with the diaphragm pressed lightly against the throat, and the switch button is depressed. The gear box output spindle is arranged to rotate at about 5,000 rpm so that the diaphragm is struck by the hammer head at a frequency of about 83 or 84 cps. The pitch of the vibrations transmitted to the users larynx is adjustable by tightening and loosening the cap on the side arm portion to compress or release the resilient material in which the diaphragm member is mounted, and to reduce or enlarge the chamber within the side arm portion between the apertured wall portion and the diaphragm. The pitch of the vibrations can thus be adjusted to suit the user's larynx, and a threaded lock ring or other suitable means can be provided for releasably securing the cap in a desired position. The cap is conveniently secured against inadvertent removal whilst such adjustments are being made.

Means can of course be provided for varying the frequency of operation of the device. Thus, the motor speed being variable in dependence on the supply voltage, this voltage can be selectively varied for example by means of a variable resistor as shown at 92 in FIG. 2 or a transistorised control circuit.

The speech aid device specifically described can of course be modified in various ways without departing from the spirit and scope of the invention.

I claim:

1. A speech device comprising a housing, a diaphragm means, means mounting said diaphragm means with one face thereof exposed as part of the outer surface of the housing for application of said face to a user's throat, a hammer means within said housing, means mounting said hammer means for movement thereof to beat against a portion of said diaphragm means within the housing, drive means for causing said hammer means to repeatedly beat against said diaphragm means, and said drive means including a motor and a resilient link between said motor and said hammer means.

2. A speech aid device according to claim 1 in which said housing comprises a tubular main body portion and a side arm portion extending therefrom, the main body portion being adapted to serve as a handle, and the diaphragm means being located at the free end of said side arm portion.

3. A speech aid device according to claim 2 in which the side arm portion has an axis at an obtuse angle to the axis of the tubular main body portion.

4. A speech aid device according to claim 3 in which the angle between the axis of the side arm portion and the tubular main body portion is at least approximately 110°.

5. A speech aid device according to claim 1 in which said hammer means is a shaft member slidably mounted in said housing with a head for beating against said portion of the diaphragm means and said motor comprises an electric motor in said housing, the speech aid device further including a switch on said housing controlling said electric motor, and said drive means further including a drive shaft rotated by said electric motor, an eccentric pin on said drive shaft, and a compression spring biasing said head toward said diaphragm means, said resilient link comprising a tension spring connecting said eccentric pin and said shaft member whereby rotation of the drive shaft causes the eccentric pin to pull and release the tension spring for compressing and releasing the compression spring for reciprocating the shaft member to alternately retract the head from said portion of said diaphragm means and propel said head against said portion.

6. A speech aid device according to claim 1 having compressive spring means adapted to oppose movement of said hammer means away from said diaphragm means.

7. A speech aid device according to claim 1 having means guiding said hammer means for axial reciprocation, and in which said motor comprises an electric motor having a rotatable drive shaft, said drive means includes an element positioned eccentrically on said drive shaft, and said resilient link comprises tensile spring means drivingly connecting said hammer means and said element.

8. A speech aid device according to claim 1 in which the hammer means comprises a shaft member having a striker head at a first end thereof, said mounting means therefor comprises an apertured wall member, said shaft member being reciprocably guided in said aperture, a first spring means is located around said shaft member and between said striker head and second wall means, said drive means comprises a spindle adapted to be rotated by said motor and a drive element eccentrically carried by said spindle for rotation therewith, and said resilient link comprises a second spring means drivingly connecting said drive element and the second end of said shaft.

9. A speech aid device according to claim 1 having means resiliently mounting said diaphragm means in an aperture in a wall of said housing.

10. A speech aid device according to claim 1 in which said housing means comprises an apertured cap member and a main body member, the cap member having a screw-threaded connection with said main body member, facing annular abutment surfaces being formed on said cap and main body members respectively, resilient washer means being located between said facing abutment surfaces, and said diaphragm means having peripheral lip means clamped by said resilient washer means.

11. A speech aid device according to claim 1 in which said drive means includes means selectively variable to alter the frequency at which said hammer means beats against said diaphragm means.

* * * * *